United States Patent [19]
Willi

[11] Patent Number: 5,658,345
[45] Date of Patent: Aug. 19, 1997

[54] ARTIFICIAL ACETABULUM AND METHOD FOR MANUFACTURE

[75] Inventor: Roland Willi, Neftenbach, Switzerland

[73] Assignee: Sulzer Medizinaltechnik AG, Switzerland

[21] Appl. No.: 500,794

[22] Filed: Jul. 11, 1995

[30] Foreign Application Priority Data

Sep. 1, 1994 [EP] European Pat. Off. .............. 94810500

[51] Int. Cl.⁶ ...................................................... A61F 2/32
[52] U.S. Cl. .................... 623/22; 29/515; 623/18
[58] Field of Search ................. 29/515, 516; 623/22, 623/23

[56] References Cited

U.S. PATENT DOCUMENTS 5,080,677  1/1992  Shelley ........................................ 623/22

FOREIGN PATENT DOCUMENTS

| 0053794 | 6/1982 | European Pat. Off. . |
|---|---|---|
| 0196946 | 10/1986 | European Pat. Off. . |
| 0297789 | 1/1989 | European Pat. Off. . |
| 0420795 | 4/1991 | European Pat. Off. . |
| 0444381 | 9/1991 | European Pat. Off. . |
| 0453694 | 10/1991 | European Pat. Off. . |
| 0578322 | 1/1994 | European Pat. Off. . |
| 2651996 | 3/1991 | France . |
| 2668923 | 5/1992 | France . |
| 2680674 | 3/1993 | France . |

*Primary Examiner*—P. W. Echols
*Assistant Examiner*—Adrian L. Coley
*Attorney, Agent, or Firm*—Townsend and Townsend and Crew LLP

[57] ABSTRACT

The acetabulum (1) in accordance with the invention comprises a spherically formed outer shell (3) as well as a spherically formed inner shell (4) which is inserted into the outer shell (3). The inner shell (4) can, for example, consist of an oxide-ceramic material, in particular of aluminum oxide. The outer shell (4) can consist of, for example, titanium. The outer surface (4c) of the inner shell (4) is formed such that it has a first partial surface (4c) with increasing outer cross-section from the pole (2a) towards the equatorial opening (4b) to a site (4a) with a largest outer diameter, that a further partial surface (4e) with an outer cross-section decreasing towards the equatorial opening (4b) connects to the partial surface (4c), which goes into a further partial surface (4f) with increasing outer cross-section towards the equatorial opening. The outer shell (3) was plastically deformed at least in the region of the partial surface (4e), so that an operative connection results between the outer shell (3) and the inner shell (4) at least over the partial surface (4e).

15 Claims, 3 Drawing Sheets

ARTIFICIAL ACETABULUM AND METHOD FOR MANUFACTURE

The invention relates to an artificial acetabulum in accordance with the an artificial acetabulum where the outer shell elastically conforms to receive a substantially non-elastic inner shell. The invention further relates to a method for manufacturing an artificial acetabulum in accordance with the invention.

BACKGROUND OF THE INVENTION

An artificial hip joint comprises a socket or joint cavity as well as a ball joint. These are made from different materials, such as, for example, oxide-ceramic materials, plastics or metals, in order to reduce the wear which occurs between the joint parts on the one hand, and to ensure a good securing of the acetabulum in the pelvic bone on the other hand. An acetabulum made from oxide-ceramic material is known from EP 0 053 794. This acetabulum, which entirely consists of oxide-ceramic material, has the disadvantage that it can only be anchored poorly into to the pelvic bone.

SUMMARY OF THE INVENTION

The object of the present invention lies in removing the present disadvantages.

This object is satisfied in accordance with providing the acetabulum with an elastic outer shell and a substantially inelastic inner shell, which defines a required spherical surface. The outer shell is elastically elongated to receive the inner shell. The acetabulum in accordance with the invention comprises at least two shells, an inner shell which is set in an outer shell. The inner shell is made in particular from an oxide-ceramic material, in particular from aluminium-oxide, however, it can also be made from a different material, such as, for example, a cobalt-chromium-alloy or from a plastic, such as polyethylene. The spherically formed inner shell has a pole and an equatorial opening on the side opposite to the pole. The outer surface of the inner shell has a partial surface towards the equatorial opening with an outer cross-section decreasing in the direction of the equatorial opening. The outer shell enters into an operative connection with the inner shell at least in this partial surface, such that the inner shell is fixedly held by the outer shell.

In the method for manufacturing an acetabulum in accordance with the invention, the spherically formed inner shell is inserted into the spherically formed outer shell in a first method step. The outer shell is plastically deformed in a second method step at least in the region which lies above the said partial surface of the inner shell, such that an operative connection results at least between the said partial surface of the inner shell and the outer shell, so that the inner shell is fixedly held by the outer shell. The plastic deformation of the outer shell occurs for example through flanging, by exercising a force on the outer shell with a corresponding tool, such that the outer shell plastically deforms.

In a particularly advantageous embodiment, the inner shell lies on the inner surface of the outer shell at least in the region of the said partial surface as well as at the pole, so that the inner shell is fixedly held. In an advantageous further embodiment of the invention, the entire outer surface of the inner shell lies on the inner surface of the outer shell.

An advantage of the present invention is to be seen in the fact that a body made from oxide-ceramic material can be used as the inner shell, the body being able to be assembled with an outer shell made from different materials, such as, for example, titanium, steel, or plastic to form an acetabulum, with the formation of the outer shell as well as the material being selectable such that the outer shell has particularly advantageous characteristics with regard to a connection to the pelvic bone.

A further advantage of the acetabulum in accordance with the invention is to be seen in the fact that the inner shell can also consist of a material such as a cobalt-chromium-alloy or of a plastic. A further shell can be arranged on and connected to the outer surface of the outer shell, for example, by welding or plastic deformation such as flanging. In this manner, an acetabulum with three or more layers can be designed which is manufactured for example from an oxide-ceramic material for the inner shell, which has a titanium shell for the outer shell, and on the outer shell of which a further shell or a further surface made from wire, for example, from titanium wire, is applied. Such an acetabulum has the advantage that the inner shell has small wear characteristics and that the layer which contacts the pelvic bone has advantageous Characteristics with regard to the growing into the pelvic bone.

Further details and advantages of the invention result from the description of embodiments of the invention by way of example with the FIGS. 1a to 3.

DESCRIPTION OF THE PREFERRED EMBODIMENT

Figure 3:
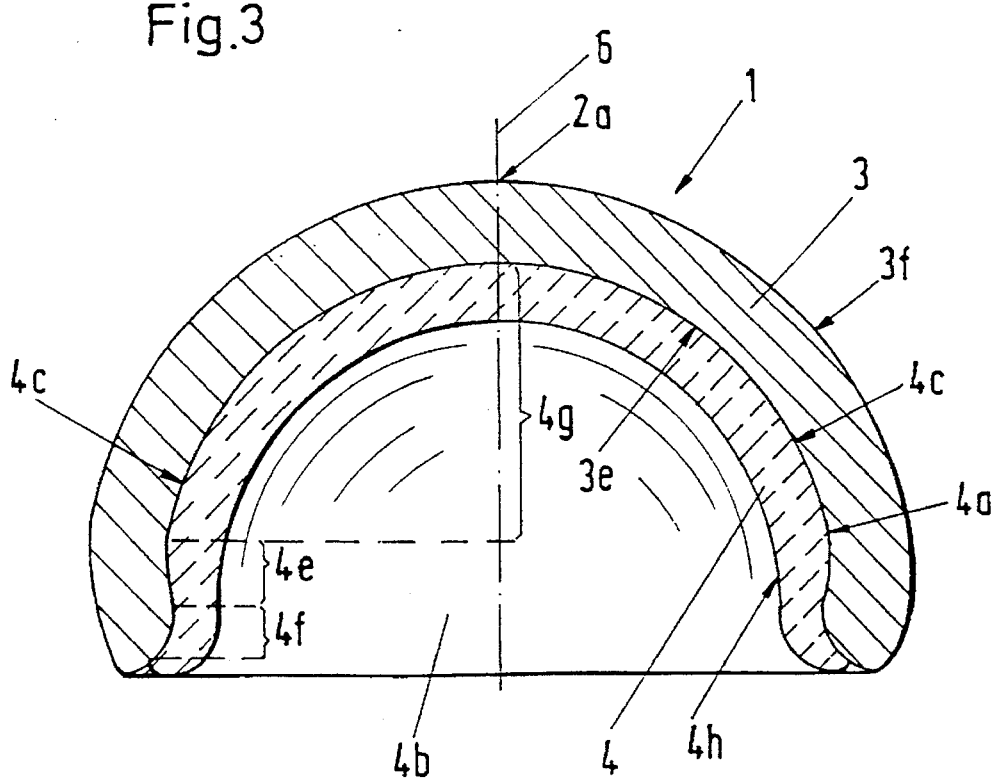
FIG. 3 is a section through a further working example of an acetabulum.

FIG. 3 shows an acetabulum in accordance with the invention having a spherically formed outer shell 3 and a spherically formed inner shell 4 which is inserted in the outer shell 3. The inner shell 4 can, for example, consist of an oxide-ceramic material, in particular of aluminium oxide. The outer shell 4 can, for example, consist of titanium. The acetabulum 1 has a pole 2a, a circular equatorial opening 4b on the opposite side, as well as an axis 6 extending through the pole 2a. The inner surface 4h of the inner shell 4 is spherically formed for receiving a ball joint. The outer shell 4c of the inner shell 4 is formed such that it has a first partial surface 4c with an increasing outer cross-section from the pole 2a towards the equatorial opening 4b, to a site 4a with a largest outer diameter which connects a further partial surface 4e to the partial surface 4c, with an outer cross-section decreasing towards the equatorial opening 4b, with the outer cross-section passing into a further partial surface 4f with increasing outer cross-section towards the equatorial opening 4b. The outer shell 3 was plastically deformed at least in the region of the partial surface 4e, so that an operative connection results between the outer shell 3 and the inner shell 4 at least over the partial surface 4e. At least three operative connections distributed about the periphery are required for a secure retaining of the inner shell 4 by the outer shell 3.

However, it can also prove to be advantageous that the outer shell 3 has an Operative connection with the inner shell 4 over the entire partial surface 4e. In the present working example, the partial surfaces 4e and 4f are formed such that a movement of the inner shell 4 is prevented in the direction of the axis 6, with the outer shell 3 exercising an operative connection on both partial surfaces 4e and 4f. It can prove to be advantageous that the entire outer surface 4c of the inner shell 4 contacts the inner surface 3e of the outer shell 3. However, it can also prove to be advantageous that the operative connection between the inner shell 4 and the outer shell 3 occurs only in the region of the partial surfaces 4e and 4f and that the remaining surfaces between the inner shell and the outer shell are spaced from one another by a gap.

Figure 1A:
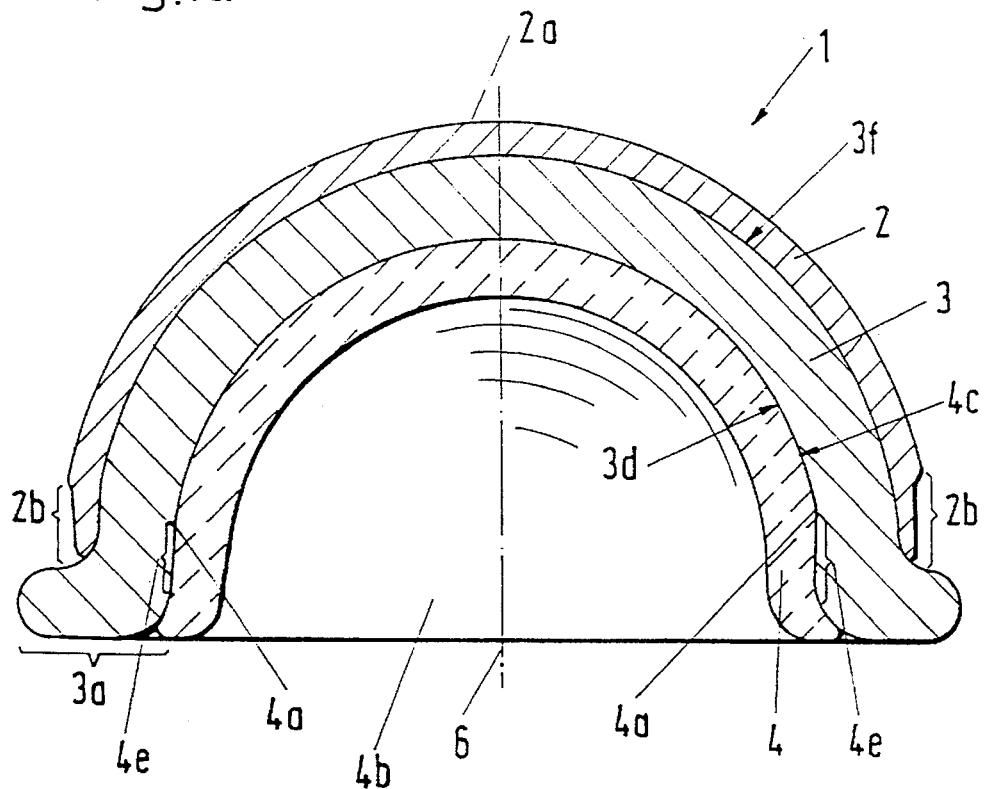
FIG. 1a is a cross-section through an acetabulum.

FIG. 1a shows a section through a further working example of an acetabulum 1 in accordance with the invention. A further shell 2 is arranged on the outer surface 3f of the outer shell 3. This further shell 2, can, for example, consist of a wire braid made from titanium wire, which has the known advantage that the bone tissue easily grows together with such a layer. In a particularly advantageous embodiment, the inner shell 4 consists of an oxide-ceramic material, the outer shell 3 consists of titanium and the further shell 2 consists of a wire braid made from titanium.

Figure 1B:
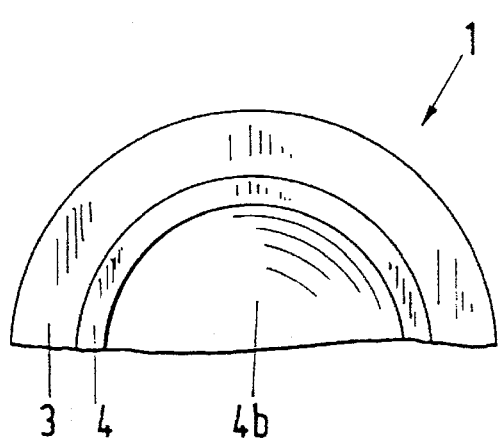
FIG. 1b is a lower view of an acetabulum in accordance with the invention.

FIG. 1b shows a lower view of the acetabulum in accordance with FIG. 1a, in which the equatorial opening 4b, the inner shell 4, as well as the outer shell 3 can be seen, with the outer shell 3 having a flange-like part 3a at the equatorial edge. An acetabulum 1 as represented in FIG. 1a is suitable for anchoring in the pelvic bone without bone cement. In this case, the outer shell 3 or the further shell 2 is inserted and secured in the pelvic bone in accordance with the known principle of a "press-fit" or a "snap-fit" socket.

Figure 1D:
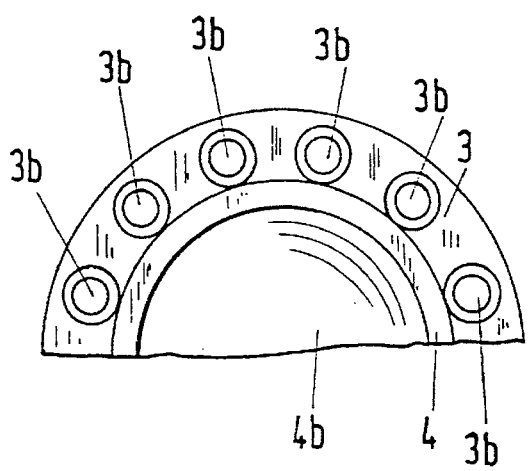
FIG. 1d is a lower view of an acetabulum of FIG. 1c.
Figure 1C:
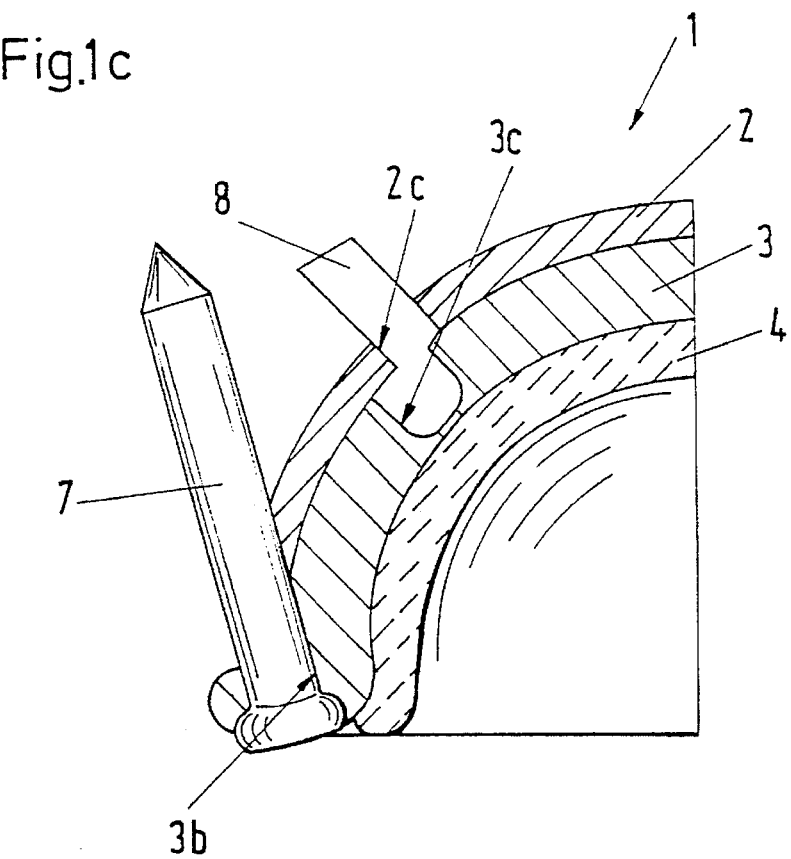
FIG. 1c is an acetabulum with arranged securing means.

FIG. 1c shows an acetabulum 1 in accordance with the invention having anchoring bodies 7, 8. The acetabulum 1 can be secured in the pelvic bone via a bone screw 7 or a nail 7, with the pelvic bone extending in the flange-like part 3a of the outer shell 3 via an aperture 3b. Furthermore, apertures 3c can be provided in the outer shell 3 and, in the case of a present further shell 2, apertures 2c can also be provided such that anchoring bodies 8, for example, elements fixedly assembled at the plant or elements which can also be assembled during the operation, can be inserted and secured.

FIG. 1d shows a lower view of an acetabulum of FIG. 1c in accordance with the invention in which the circular equatorial opening 4b, the inner shell 4, the outer shell 3, as well as the apertures 3b for receiving a securing means 7 can be seen.

Figure 2A:
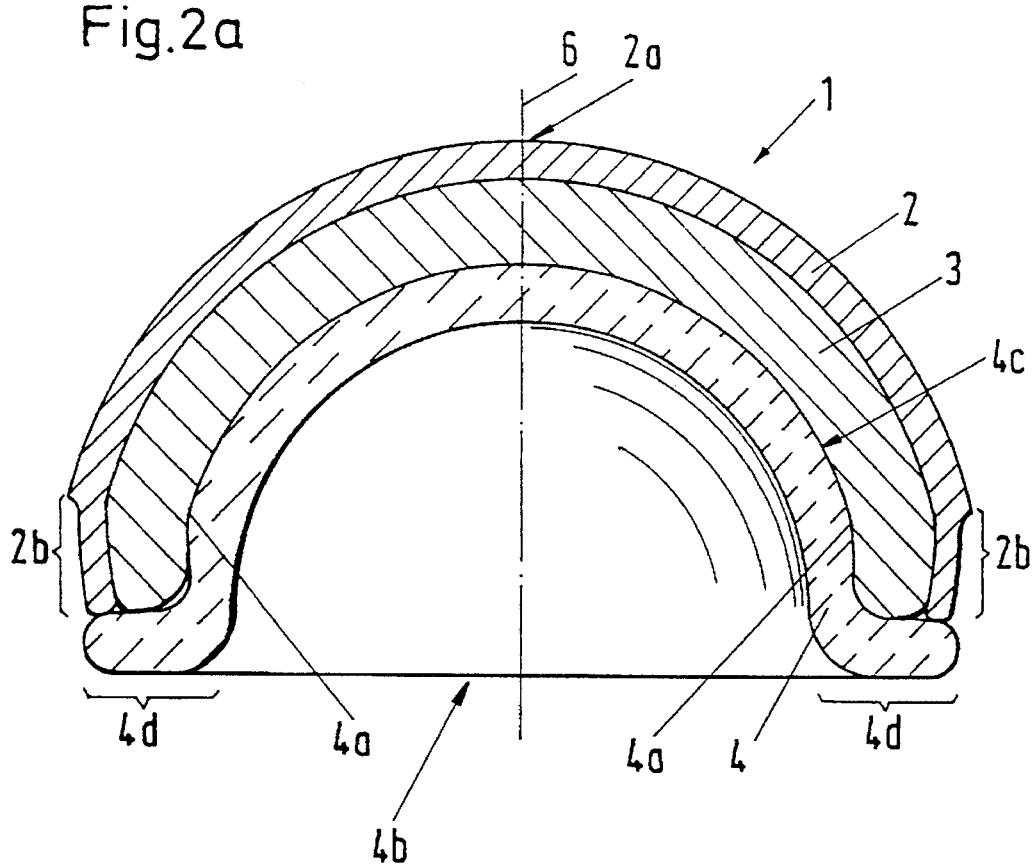
FIG. 2a is a section through a further embodiment of an acetabulum.

FIG. 2a shows a further working example of an acetabulum 1 in accordance with the invention which has a flange-like part 4d at the equatorial edge, which extends radially to the axis 6. Such a flange-like part 4d has the advantage that, if the inner shell 4 is manufactured from an oxide-ceramic material, the flange-like part 4d guides the insertion of the joint ball. It is known that in particular oxide-ceramic joint balls are very sensitive to injury during the insertion into the acetabulum. In the present working example, a joint ball is set on the flange-like part 4d and now glides on the oxide-ceramic layer into the interior of the inner shell 4, so that an injury of the oxide-ceramic joint balls is ruled out through projecting, metallic parts.

Figure 2B:
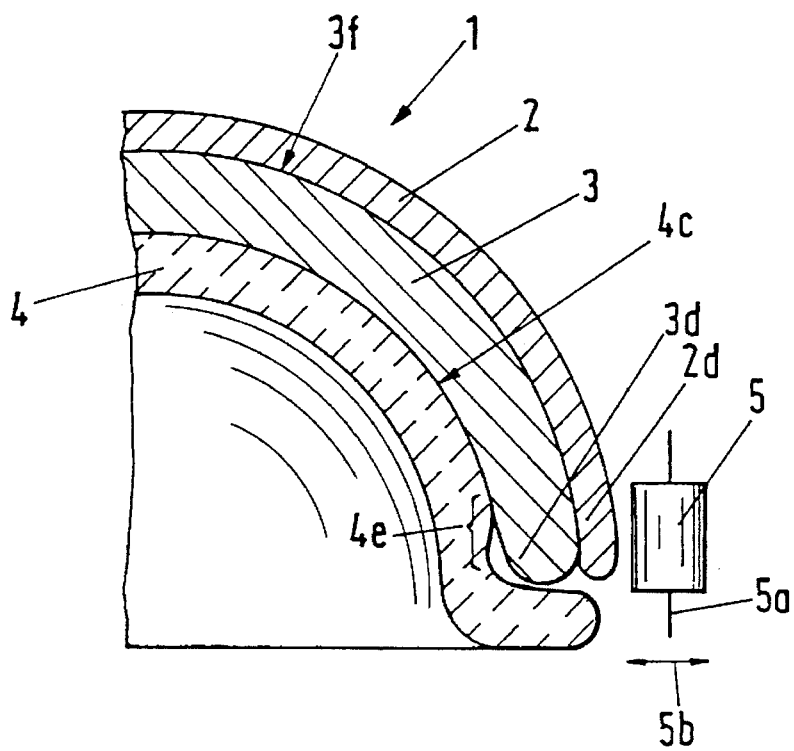
FIG. 2b is a detail view for manufacturing an acetabulum, before the plastic deformation of the outer shell.

The method for manufacturing an acetabulum 1 in accordance with the invention is represented in FIG. 2b. The spherically formed inner shell 4 is inserted in the spherically formed outer shell 3. A further shell 2 or layer 2d is arranged on the outer surface 3f of the outer shell 3. After inserting the inner shell 4 into the outer shell 3, the outer shell 3 is plastically deformed by a device 5 at least in the region of the partial surface 4e, such that the exposed part 3d of the outer shell 3 is plastically deformed by the forces acting in radial operation and that the exposed part 3d of the outer shell 3 lies on the outer surface 4c of the inner shell 4. In the present working example, the plastic deformation is effected through flanging by moving a cylindrical body which can be pivoted about an axis of a rotation 5a in the direction of movement 5b towards the acetabulum 1, thus acting on the further layer 2d and thus indirectly also acting on the exposed part 3d of the outer shell 3. This effects a plastic deformation of the further shell 2 as well as of the outer shell 3, as is for example represented in FIG. 2a by the flanged region 2b of the further shell 2. This effects a further retaining of the further shell 2 to the outer shell 3, and a defined transition between the inner shell 4 and the further shell 2 or layer 2d can be generated so that the two shells 4 and 2, for example, pass into one another without a step.

A plurality of methods are known which permit a plastic deformation of bodies so that the working example shown in FIG. 2b with a method by flanging should be viewed only as one of a plurality of methods which are suitable in order to connect an outer shell 3 to an inner shell 4 by plastic deformation.

I claim:

1. An artificial acetabulum (1) comprising:
    at least one spherically formed elastic outer shell (3) and at least one substantially inelastic inner shell (4);
    the elastic outer shell (3) having a pole (2a) and defining an equatorial opening (4b) with an inner surface of the elastic outer shell (3) having a partial surface with an inner cross-section decreasing toward an equatorial opening;
    the inelastic inner shell (4) having an outer surface (4c) with a partial surface (4e) with an outer cross-section decreasing towards the equatorial opening of the inner shell;
    the inner shell (4) being inserted into the outer shell (3) to elastically deform the outer shell (3) of the partial surface (4e) of the inner shell to generate an operative connection between the outer shell (3) and the partial surface (4e) so that the inner shell (4) is fixedly held by the outer shell (3).

2. An acetabulum (1) in accordance with claim 1 and further comprising:
    the inner shell (4) having a flange-like part (4d) at the equatorial opening (4b), with the flange-like part (4d) projecting beyond the outer shell (3).

3. An acetabulum (1) in accordance with claim 1 and further including:
    a further shell (2) lying on an outer surface (3f) of the outer shell (4) and attached to the outer shell (4).

4. An acetabulum (1) in accordance with claim 3, and further including:
    the further shell (2) consists of titanium or steel, in particular formed as a wire braid.

5. An acetabulum (1) in accordance with claim 1 and further comprising:
    the inner shell (4) and/or the outer shell (3) has apertures (3b) for receiving securing means.

6. An acetabulum (1) in accordance with claim 1 and wherein:
    the outer shell (3) has apertures (3c) at its surface (3f) for receiving anchoring bodies (8).

7. Method for manufacturing an acetabulum (1) with a pole (2a), as well as an equatorial opening (4b) comprising the steps of:

providing at least one spherically formed elastic outer shell (3) with an inner surface of the elastic outer shell having a partial surface with an inner cross-section decreasing toward the equatorial opening;

providing a substantially inelastic inner shell (4), with an outer surface (4c) of the inner shell (4) having a partial surface (4e) with an outer cross-section decreasing towards the equatorial opening (4b);

inserting the inner shell (4) into the outer shell (3), elastically deforming the outer shell (3) at least at the partial surface (4e), in order to generate an operative connection between the outer shell (3) and the partial surface (4e), so that the inner shell (4) is fixedly held by the outer shell (3).

8. Method for manufacturing an acetabulum (1) with a pole (2a), as well as an equatorial opening (4b) according to claim 9 comprising the further steps of:

providing a further shell (2) capable of elastic deformation in the vicinity of the equatorial opening (4b);

applying the further shell (2) to the outer shell (3), elastically deforming the further shell (2) such that the further shell (2) is fixedly connected to the outer shell (3).

9. Method for manufacturing an acetabulum (1) with a pole (2a), as well as an equatorial opening (4b) according to claim 8 comprising the further steps of:

further shell (2) is of a material selected from the group consisting of titanium, steel, and a wire braid.

10. Method for manufacturing an acetabulum (1) with a pole (2a), as well as an equatorial opening (4b) according to claim 7 comprising the further steps of:

the provided inner shell (4) consists of a material selected from the group consisting of a ceramic material, and a cobalt-chromium-alloy.

11. Method for manufacturing an acetabulum (1) with a pole (2a), as well as an equatorial opening (4b) according to claim 7 comprising the further steps of:

the provided inner shell (4) has a flange-like part (4d) at the equatorial opening (4b), with the flange-like part (4d) projecting beyond the outer shell (3).

12. Method for manufacturing an acetabulum (1) with a pole (2a), as well as an equatorial opening (4b) according to claim 7 comprising the further steps of:

the provided outer shell (3) consists of titanium, or steel.

13. Method for manufacturing an acetabulum (1) with a pole (2a), as well as an equatorial opening (4b) according to claim 7 comprising the further steps of:

the provided inner shell (4) and/or the outer shell (3) has apertures (3b) for receiving securing means, such as bone screws (7).

14. Method for manufacturing an acetabulum (1) with a pole (2a), as well as an equatorial opening (4b) according to claim 7 comprising the further steps of:

the provided outer shell (3) has apertures (3c) at its surface (3f) for receiving anchoring bodies (8).

15. The product of the process of claim 7.

* * * * *